United States Patent [19]

Brittelli et al.

[11] Patent Number: 4,977,173

[45] Date of Patent: * Dec. 11, 1990

[54] AMINOMETHYL OXOOXAZOLIDINYL ETHENYLBENZENE DERIVATIVES USEFUL AS ANTIBACTERIAL AGENTS

[75] Inventors: David R. Brittelli, Nottingham, Pa.; Peter F. Corless, Southborough, Mass.; Walter A. Gregory; Chung-Ho Park, both of Wilmington, Del.

[73] Assignee: E. I. Du Pont de Nemours and Company, Wilmington, Del.

[ * ] Notice: The portion of the term of this patent subsequent to Nov. 10, 2004 has been disclaimed.

[21] Appl. No.: 376,457

[22] Filed: Jul. 7, 1989

Related U.S. Application Data

[63] Continuation of Ser. No. 110,837, Oct. 21, 1987, abandoned.

[51] Int. Cl.$^5$ ............................................ C07D 263/20
[52] U.S. Cl. .................................... 514/376; 548/229; 548/232; 548/234
[58] Field of Search ...................... 548/229, 232, 234; 514/376

[56] References Cited

U.S. PATENT DOCUMENTS

| | | | |
|---|---|---|---|
| Re. 29,607 | 4/1978 | Fauran et al. | 548/229 |
| 3,687,965 | 8/1972 | Fauran et al. | 548/229 |
| 4,128,654 | 12/1978 | Fugitt et al. | 514/376 |
| 4,250,318 | 2/1981 | Dostert et al. | 548/229 |
| 4,340,606 | 7/1982 | Fugitt et al. | 514/376 |
| 4,461,773 | 7/1984 | Gregory | 514/376 |
| 4,476,136 | 10/1984 | Dostert et al. | 548/229 |
| 4,705,799 | 10/1987 | Gregory | 548/229 |
| 4,801,600 | 1/1989 | Wong | 548/234 |

FOREIGN PATENT DOCUMENTS 0127902 12/1984 European Pat. Off. .
0184170 6/1986 European Pat. Off. .
2094299 9/1982 United Kingdom .

*Primary Examiner*—Donald G. Daus
*Attorney, Agent, or Firm*—Robert W. Black; Gildo E. Fato

[57] ABSTRACT

Aminomethyl oxooxazolidinyl ethenylbenzene derivatives, including the nitriles, sulfoxides, acetamides and nitro compounds, such as l-N-[3-[4-(E-1-methyl-2-cyanoethenyl)phenyl]-2-oxooxazolidin-5-ylmethyl-]acetamide, possess useful antibacterial activity.

42 Claims, No Drawings

AMINOMETHYL OXOOXAZOLIDINYL ETHENYLBENZENE DERIVATIVES USEFUL AS ANTIBACTERIAL AGENTS

This application is a continuation of application Ser. No. 07/110,837, filed Oct. 21, 1987, now abandoned.

TECHNICAL FIELD

This invention relates to novel aminomethyl oxooxazolidinyl ethenylbenzene derivatives, their preparation, to pharmaceutical compositions containing them, and to methods of using them to alleviate bacterial infections.

BACKGROUND OF THE INVENTION

At the present time, no existing antibacterial product provides all features deemed advantageous. There is continual development of resistance by bacterial strains. A reduction of allergic reactions and of irritation at the site of injection, and greater biological half-life (i.e., longer in vivo activity) are currently desirable features for antibacterial products.

U.S. Pat. No. 4,128,654 issued to Fugitt et al. on Dec. 5, 1978, discloses, among others, compounds of the formula:

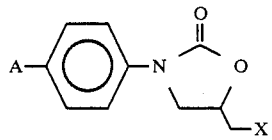

where
A=RS(O)$_n$;
X=Cl, Br or F;
R=C$_1$-C$_3$ alkyl; and
n=0, 1 or 2.

The compounds are disclosed as being useful in controlling fungal and bacterial diseases of plants.

U.S. Reissue Pat. No. 29,607 reissued Apr. 11, 1978 discloses derivatives of 5-hydroxymethyl-3-substituted-2-oxazolidinones of the formula:

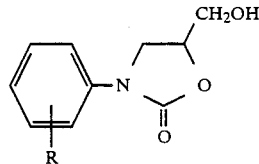

where R is H, F, CH$_3$, or CF$_3$. Such compounds are described as having antidepressive, tranquilizing, sedative, and antiinflammatory properties.

U.S. Pat. No. 4,250,318, which was issued on Feb. 10, 1981, discloses antidepressant compounds of the formula:

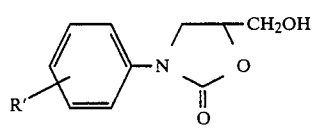

where R' can be, among others, a para-n-pentylamino group, an SR$_1$ group where R$_1$ is C$_1$-C$_5$ alkyl, or an acetylmethylthio group.

U.S. Pat. No. 4,340,606, issued to Fugitt et al. on Jul. 20, 1982, discloses antibacterial agents of the general formula:

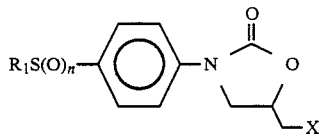

where
R$_1$=CH$_3$, C$_2$H$_5$, CF$_2$H, CF$_3$ or CF$_2$CF$_2$H; and
X=OR$_2$ (R$_2$=H or various acyl moieties).

U.S. Pat. No. 3,687,965, issued to Fauran et al. on Aug. 29, 1972, discloses compounds of the formula:

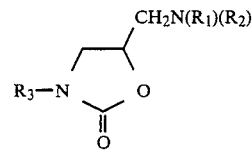

where
—N(R$_1$) (R$_2$) represents either dialkylamino radical in which the alkyl portions have one to five carbon atoms, or a heterocyclic amino radical which may be substituted by an alkyl radical having one to five carbon atoms or by a pyrrolidinocarbonylmethyl radical, and R$_3$ represents a phenyl radical which may be substituted by one or more of the following radicals:
an alkoxy radical having one to five carbon atoms;
a halogen atom;
a trifluoromethyl radical, or
a carboxyl radical which may be esterified.

The patent states that these compounds possess hypotensive, vasodilatatory, spasmolytic, sedative, myorelaxant, analgesic and antiinflammatory properties. There is no mention of antibacterial properties.

Belgian Patent No. 892,270, published Aug. 25, 1982, discloses monoamine oxidase inhibitors of the formula

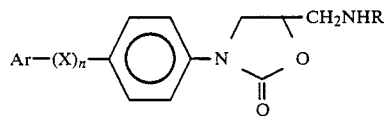

where
R is H, C$_1$-C$_4$ alkyl or propargyl;
Ar is phenyl, optionally substituted by halo or trifluoromethyl;
n is 0 or 1; and
X is —CH$_2$CH$_2$—, —CH=CH—, an acetylene group or —CH$_2$O—.

U.S. Pat. No. 4,461,773 issued to W. A. Gregory on Jul. 24, 1984 discloses antibacterial agents of the formula

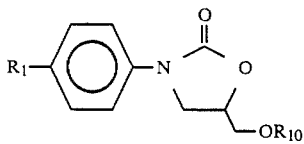

wherein, for the l, and mixtures of the d and l stereoisomers of the compound, $R_1$ is $R_2SO_2$,

or

$R_2$ is $-NR_3R_4$, $-N(OR_3)R_4$, $-N_3$, $-NHNH_2$, $-NX_2$, $-NR_6X$, $-NXZ$,

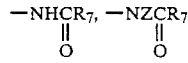

or
$-N=S(O)_nR_8R_9$;

$R_3$ and $R_4$ are independently H, alkyl of 1–4 carbons or cycloalkyl of 3–8 carbons;

$R_5$ is $NR_3R_4$ or $OR_3$;

$R_6$ is alkyl of 1–4 carbons;

$R_7$ is alkyl of 1–4 carbons, optionally substituted with one or more halogens;

$R_8$ and $R_9$ are independently alkyl of 1–4 carbons or, taken together are $-(CH_2)_p-$;

$R_{10}$ is H, alkyl of 1–3 carbons,

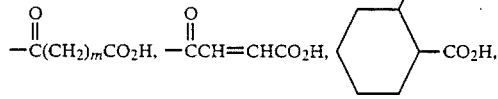

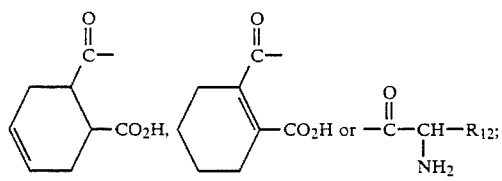

$R_{11}$ is alkyl of 1–12 carbons;
$R_{12}$ is H, alkyl of 1–5 carbons, $CH_2OH$ or $CH_2SH$;
X is Cl, Br or I;
Z is a physiologically acceptable cation;
m is 2 or 3;
n is 0 or 1; and p is 3, 4 or 5; and when $R_{10}$ is alkyl of 1–3 carbons, $R_1$ can also be $CH_3S(O)_q$ where q is 0, 1 or 2; or a pharmaceutically acceptable salt thereof.

European Patent Application No. 127,902, published Dec. 12, 1984, and 184,170, published Jun. 11, 1986, disclose antibacterial agents of the formula:

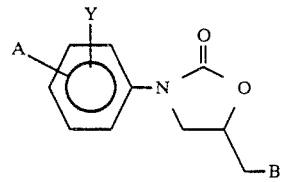

wherein, for the l, and mixtures of the d and l stereoisomers of the compound,

A is $-NO_2$, $-S(O)_nR_1$, $-S(O)_2-N=S(O)_pR_2R_3$, $-SH$,

$-COR_{23}$, $-COR_{25}$, $-CONR_5R_6$,

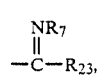

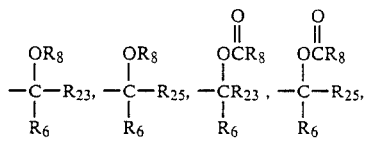

$-CN$, $-OR_5$, halogen, $-NR_5R_6$,

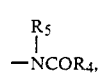

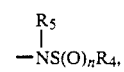

$CR_{23}(OR_{16})OR_{17}$,

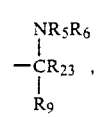

alkyl of 1 to 8 carbons, optionally substituted with one or more halogen atoms, OH, =O other than at alpha position, $S(O)_nR_{24}$, $NR_5R_6$, alkenyl of 2–5 carbons, alkynyl of 2–5 carbons or cycloalkyl of 3–8 carbons;

$R_1$ is $C_1$–$C_4$ alkyl, optionally substituted with one or more halogen atoms, OH, CN, $NR_5R_6$ or $CO_2R_8$; $C_2$–$C_4$ alkenyl; $-NR_9R_{10}$; $-N_3$;

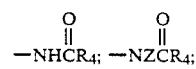

$-NX_2$; $NR_9X$ $-NXZ^+$;

$R_2$ and $R_3$ are independently $C_1$-$C_2$ alkyl or, taken together are —$(CH_2)_q$—;

$R_4$ is alkyl of 1-4 carbons, optionally substituted with one or more halogens;

$R_5$ and $R_6$ are independently H, alkyl of 1-4 carbons or cycloalkyl of 3-8 carbons;

$R_7$ is —$NR_5R_6$, —$OR_5$ or $$-NHCR_5\overset{O}{\underset{\|}{}}$$

$R_8$ is H or alkyl of 1-4 carbons;

$R_9$ is H, $C_1$-$C_4$ alkyl or $C_3$-$C_8$ cycloalkyl;

$R_{10}$ is H, $C_1$-$C_4$ alkyl, $C_2$-$C_4$ alkenyl, $C_3$-$C_4$ cycloalkyl, —$OR_8$ or —$NR_{11}R_{11A}$;

$R_{11}$ and $R_{11A}$ are independently H or $C_1$-$C_4$ alkyl, or taken together, are —$(CH_2)_r$—;

X is Cl, Br or I;

Y is H, F, Cl, Br, alkyl of 1-3 carbons, or $NO_2$, or A and Y taken together can be —O—$(CH_2)_t$O—;

Z is a physiologically acceptable cation;

n is 0, 1 or 2;

p is 0 or 1;

q is 3, 4 or 5;

r is 4 or 5;

t is 1, 2 or 3;

B is —$NH_2$, $$-\underset{\underset{R_{12}}{|}}{N}-\underset{\underset{}{}}{\overset{\overset{O}{\|}}{C}}-R_{13}, \quad -\underset{\underset{R_{12}}{|}}{N}-S(O)_uR_{14},$$

or $N_3$;

$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms; $C_2$-$C_4$ alkenyl; $C_3$-$C_4$ cycloalkyl; phenyl; —$CH_2OR_{15}$; —$CH(OR_{16})OR_{17}$; —$CH_2S(O)_vR_{14}$;

$$\overset{O}{\underset{\|}{CR_{15}}};$$

—$OR_{18}$; —$SR_{14}$; —$CH_2N_3$; the aminoalkyl groups derived from α-amino acids such as glycine, L-alanine, L-cysteine, L-proline, and D-alanine; —$NR_{19}R_{20}$; or $C(NH_2)R_{21}R_{22}$;

$R_{14}$ is $C_1$-$C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are —$(CH_2)_m$—;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl, phenyl or, taken together, are —$(CH_2)_s$—;

u is 1 or 2;

v is 0, 1 or 2;

m is 2 or 3;

s is 2, 3, 4 or 5; and $R_{23}$ is H, alkyl of 1-8 carbons optionally substituted with one or more halogens, or cycloalkyl of 3-8 carbons;

$R_{24}$ is alkyl of 1-4 carbons or cycloalkyl of 3-8 carbons;

$R_{25}$ is alkyl of 1-4 carbons substituted with one or more of —$S(O)_nR_{24}$; —$OR_8$, $$-OCR_8\overset{O}{\underset{\|}{}},$$

—$NR_5R_6$, or alkenyl of 2-5 carbons optionally substituted with CHO; or a pharmaceutically suitable salt thereof; provided that:

(1) when A is $CH_3S$—, then B is not $$-\underset{\underset{CH_3}{|}}{N}-CO_2CH_3;$$

(2) when A is $CH_3SO_2$—, then B is not $$-\underset{\underset{CH_3}{|}}{N}-COCH_3 \quad \text{or} \quad -\underset{\underset{CH_3}{|}}{N}-COCF_3;$$

(3) when A is $H_2NSO_2$— and B is $$-\underset{\underset{R_{12}}{|}}{N}-\overset{\overset{O}{\|}}{C}R_{13},$$

then $R_{12}$ is H;

(4) when A is —CN, B is not —$N_3$;

(5) when A is $(CH_3)_2CH$, B is not $NHCOCH_2Cl$;

(6) when A is $OR_5$, then B is not $NH_2$;

(7) when A is F, then B is not $NHCO_2CH_3$.

None of the above-mentioned references suggest the novel antibacterial compounds of this invention.

SUMMARY OF THE INVENTION

According to the present invention, there is provided an oxazolidinone of the formula:

(I)

wherein for the l isomer or racemic mixtures containing it

B is $NH_2$, $$-\underset{\underset{R_4}{|}}{N}-\overset{\overset{O}{\|}}{C}-R_5, \quad -\underset{\underset{R_4}{\diagdown}}{N}-S(O)_uR_6,$$

or $N_3$ u is 1 or 2:

$R_4$ is H, alkyl of 1-10 carbon atoms, or cycloalkyl of 3-8 carbon atoms;

$R_5$ is H, alkyl of 1-4 carbon atoms optionally substituted with one or more halogen atoms, alkenyl of 2-4 carbon atoms, cycloalkyl of 3-4 carbon atoms, phenyl; $OR_6$, or $CH_2OR_4$;

$R_6$ is alkyl of 1-4 carbon atoms optionally substituted with one or more halogen atoms;

$R_7$ is H, $CH_3$, $C_2H_5$, F or OH;

$R_1$ independently is H, $CF_3$, alkyl of 1-3 carbon atoms optionally substituted with one halogen, phenyl, or phenyl optionally substituted with one or more halogen atoms, or taken together with $R_2$ forms a 5-, 6-, or 7-membered ring of the formula:

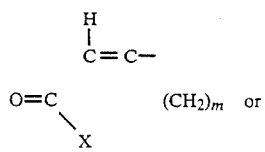

—$(CH_2)_p$—, when $R_3$ is an electron-withdrawing group;

$R_2$ and $R_3$ independently are an electron-withdrawing group, H, $CF_3$, alkyl of 1–3 carbon atoms optionally substituted with one halogen, or phenyl, provided at least one of $R_2$ or $R_3$ is an electron-withdrawing group, or $R_2$ and $R_3$ taken together form a 5, 6 or 7-membered ring of the formula:

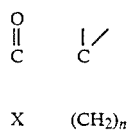

m is 1, 2 or 3;
n is 2, 3 or 4;
p is 3, 4 or 5; and

X is $CH_2$, O, S, or NR where R is H or alkyl of 1–5 carbon atoms; or a pharmaceutically suitable salt thereof.

Also provided is a pharmaceutical composition consisting essentially of a suitable pharmaceutical carrier and a compound of Formula (I) and a method of using a compound of Formula (I) to treat bacterial infection in a mammal.

Further provided is a process for preparing compounds of Formula (I), such a process being described in detail hereinafter.

PREFERRED EMBODIMENTS

Preferred compounds are the oxazolidinones of Formula (I) where:
(a) B is

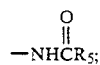

where $R_5$ is H, $CH_3$, $OR_6$, $CHCl_2$, $CH_2Cl$, $CH_2OH$ or $CH_2OCH_3$; or (b) $R_1$ independently is H or alkyl of 1–3 carbon atoms, or is taken together with $R_2$ to form a 5- or 6-membered ring of the formula:

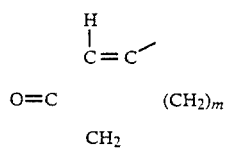

where m is 1 or 2; or (c) $R_2$ independently is an electron-withdrawing group; or (d) $R_3$ independently is H, alkyl of 1–3 carbon atoms or phenyl.

More preferred compounds are the oxazolidinones of Formula (I) where:
(a) B is

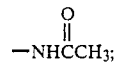

or (b) $R_1$ independently is H, $CH_3$ or $C_2H_5$, or is taken together with $R_2$ to form a 5- or 6-membered ring of the formula:

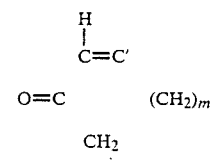

where m is 1 or 2; or (c) $R_2$ independently is CN or $NO_2$; or
(d) $R_3$ independently is H, $CH_3$ or $C_2H_5$ Specifically preferred are the following compounds:
(l)-N-[3-[4-(E-1-methyl-2-cyanoethenyl)-phenyl]-2-oxooxazolidin-5-ylmethyl]acetamide;
(l)-N-[3-[4-(3-oxo-1-cyclohexen-1-yl)phenyl]-2-oxooxazolidin-5-ylmethyl]acetamide;
(l)-N-[3-[4-(E-2-nitroethenyl)phenyl]-2-oxooxazolidin-5-ylmethyl]acetamide;
(l)-N-[3-[4-(E-1-methyl-2-nitroethenyl)-phenyl]-2-oxooxazolidin-5-ylmethyl]acetamide

DETAILED DESCRIPTION

The compounds of Formula (I) contain at least one chiral center, and as such exist as two individual isomers or as a mixture of both. This invention relates to the levorotatory isomer (l) which for many of the compounds in this invention can be referred to as the (S) isomer, as well as mixtures containing both the (R) and (S) isomers. Additional chiral centers may be present in any of the R groups and/or B and this invention relates to all possible stereoisomers in these groups.

For the purposes of this invention, the l-isomer of compounds of Formula (I) is intended to mean compounds of the configuration depicted; when B is NHAc, and closely related groups, this isomer is described as the (S)-isomer in the Cahn-Ingold-Prelog nomenclature:

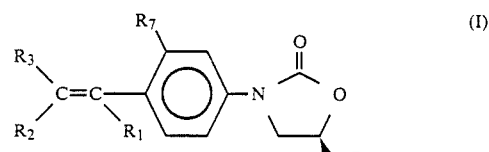

Furthermore, a different type of stereoisomerism exists when the compounds of Formula (I) contain groups $R_1$ and $R_2$ which are different. Such isomers which may be interconverted by torsion around double bonds. are classically termed geometric isomers or cis-trans-isomers. The newer method of describing them is based on the Cahn-Ingold-Prelog system by which two groups at each carbon atom of the double bond are ranked by the sequence rules. Then that isomer with two higher ranking groups on the same side of the double bond is called Z (for the German word zusammen meaning together); the other is E (for entgegen meaning opposite). This invention relates to both E- or Z-isomers separately or mixed together.

The concept of the electron-withdrawing group derives from consideration of the effect of substituents on the rate of various reactions. The constant $\sigma$ may be defined, which is characteristic for a particular group. The $\sigma$ values are numbers which sum up the total electrical effects (field plus resonance) of a group. A positive value of $\sigma$ indicates an electron-withdrawing group. Different $\sigma$ values have been developed for different positions on the benzene ring; we choose $\sigma_p$ as most appropriate for defining the class of substituents operable in this application. (A discussion of the concept of electron-withdrawing groups may be found in: J. March, Advanced Organic Chemistry, Reactions, Mechanisms, and Structure, 2nd Edition, McGraw-Hill, New York, 1977, Chapters 2 and 9, as well as other standard texts on advanced organic chemistry).

The substituents conferring particular antibacterial activity to the subject compounds of this application are unsaturated functional groups having $\sigma_p$ greater than about 0.20. A listing of groups and their $\sigma_p$ constants may be found in C. Hansch and A. Leo, Substituent Constants for Correlation Analysis in Chemistry and Biology, John Wiley and Sons, New York, 1979. Some representative examples of electron-withdrawing groups are the nitro (—NO$_2$), cyano (—CN), formyl (—CHO), carboxamido (—C(=O)NH$_2$), N-methyl carboxamido (—C(=O)NHCH$_3$), acetyl (—C(=O)CH$_3$), propionyl (—C(=O)C$_2$H$_5$), carbomethoxy (—C(=O)OCH$_3$), methylsulfinyl (—S(O)CH$_3$), methylsulfonyl (—SO$_2$CH$_3$), fluoromethylsulfinyl(—SOCH$_2$F), trifluoromethylsulfonyl (—SO$_2$CF$_3$), and dimethylphosphinyl (—PO(CH$_3$)$_2$) groups.

SYNTHESIS

Compounds of Formula (I) can be prepared as follows:

Scheme 1:

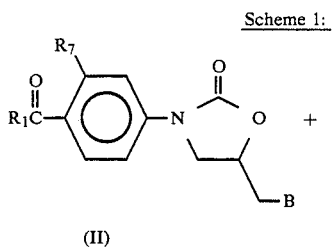

(II)

-continued
Scheme 1:

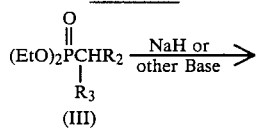

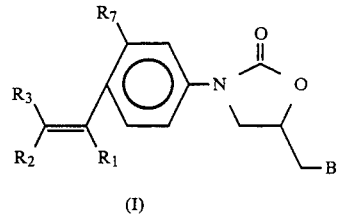

(I)

Wherein R$_1$ independently is H, CF$_3$, alkyl of 1–3 carbon atoms optionally substituted with one halogen, or phenyl. R$_2$ and R$_3$ independently are H, CF$_3$, alkyl of 1–3 carbon atoms optionally substituted with one halogen, phenyl or CN, provided that only one of R$_2$ and R$_3$ is CN and B is as described previously; provided, R$_5$ in B is not one carbon atom substituted with one or more halogen atoms.

Solvents such as 1,2-dimethoxyethane, dioxane, bis-(2-methoxyethyl)ether, N,N-dimethylformamide (DMF), N,N-dimethylacetamide (DMAc), acetonitrile, ethanol or other alcohols may be used. Suitable bases include sodium hydride, butyllithium or an alkoxide. The reaction is typically carried out by adding a base to a solution of the phosphonate (III) at 0° to 20° C. followed by addition of the substrate (II). The reaction mixture is stirred from about room temperature to 60° C. for 1 to 20 hours, the solvent is removed under reduced pressure and the residue is triturated with water. The resulting crude product which is usually a mixture of E and Z isomers with E isomer predominant, is separated and purified by conventional means. The starting compound (II) may be dl- (the racemate) or the l-isomer.

The compounds of Formula (II) are prepared by the process previously described in published European applications 127,902 and 184,170. Compounds wherein R$_5$ is one carbon atom substituted with one or more halogen atoms can be prepared by reaction of compound (I) (B is NH$_2$)· with one or more halogen-substituted acetyl chlorides or acetic anhydrides in the presence of a base. Solvents such as 1,2-dimethoxyethane, dioxane, acetonitrile, tetrahydrofuran, or DMF may be used. Suitable bases include triethylamine or pyridine.

Scheme 2:

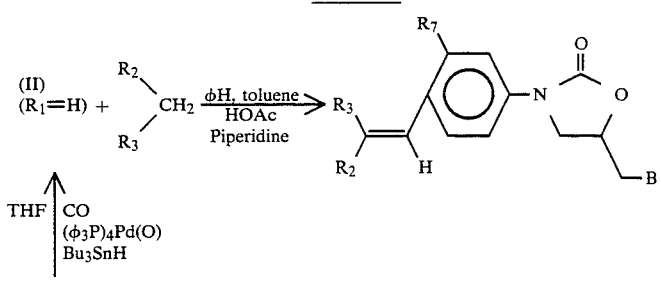

Scheme 2:

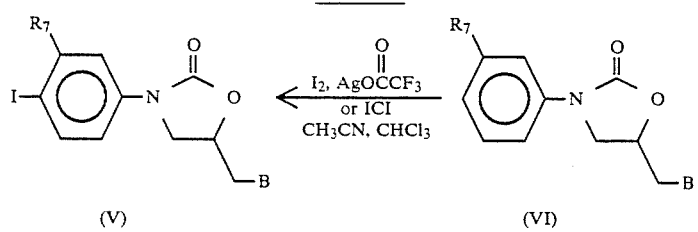

Compounds of Formula (I) which may be prepared using the procedures of Scheme 2 are those where $R_1$ is H, and $R_2$ and $R_3$ independently are both electron-withdrawing groups previously defined except that when one of $R_2$ or $R_3$ is $NO_2$, the remaining $R_2$ or $R_3$ group can be an electron-withdrawing group including another $NO_2$ group or H, $CF_3$, alkyl of 1–3 carbon atoms optionally substituted with one or more halogen atoms, or phenyl. The reaction is typically carried out in an aprotic solvent such as benzene or toluene under reflux in the presence of catalytic amounts of a carboxylic acid such as acetic acid and an amine such as piperidine with azeotropic removal of water. The solvent is then removed under reduced pressure and the desired product is isolated as previously described.

Compounds of Formula (VI) are iodinated using iodine and silver trifluoroacetate or iodine monochloride in solvents such as chloroform, acetonitrile, acetic acid or mixtures of solvents thereof at 0° to 60° C. After the reaction mixture is stirred for 1 to 24 hours, the resulting silver halide was filtered off, the solvent was removed under reduced pressure and the residue was triturated with distilled water. The crude product obtained by filtration is purified by recrystallization from suitable solvents such as acetonitrile with the aid of activated charcoal. The iodocompounds (V) are then converted to the aldehydes (II) by addition of carbon monoxide in suitable solvents such as toluene, THF, glyme and DMF or mixtures thereof at 10° to 70° C. in the presence of tributyltin hydride and tetrakis(triphenylphosphine)palladium(O).

Scheme 3:

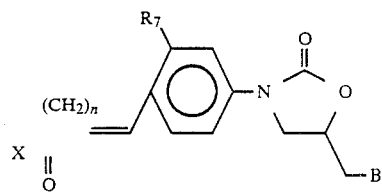

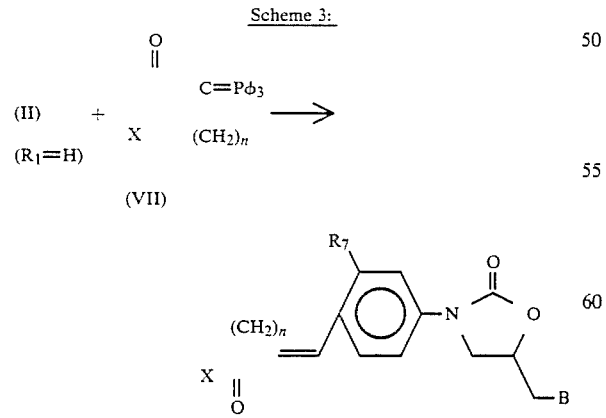

Compounds of Formula (I) where $R_1$ is H, and $R_2$ and $R_3$ are taken together to form a 5, 6 or 7-membered ring of formula:

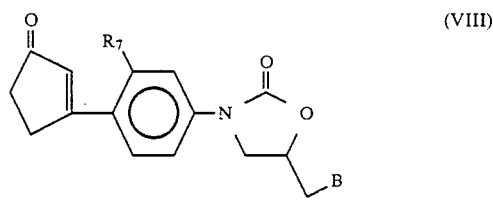

where n is 2, 3, or 4; X is $CH_2$, O, S, or NR where R is H or alkyl of 1–5 carbon atoms, or a pharmaceutically suitable salt thereof, may be prepared by reaction of the cyclic ylides of Formula (VII) with compounds of Formula (II) in Scheme 3. The cyclic ylides of Formula (VII) can be prepared by procedures describe in H. O. House and H. Barad, *J. Org. Chem.*, 28, 90 (1963).

Compounds of Formula (I) where $R_1$ is taken together with $R_2$ to form a 5-membered ring of Formula (VIII)

(VIII)

may be prepared according to synthetic Scheme 4.

Scheme 4:

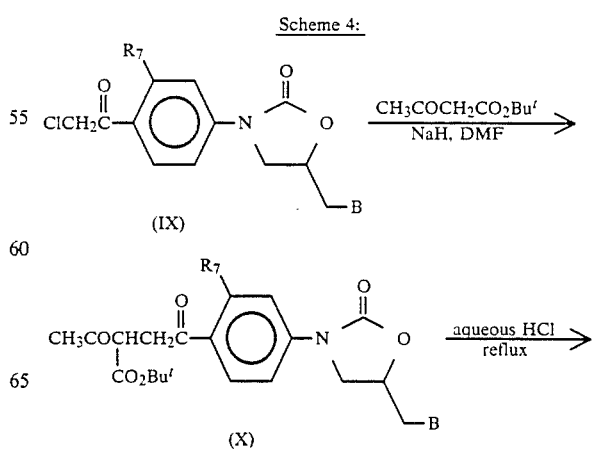

-continued
Scheme 4:

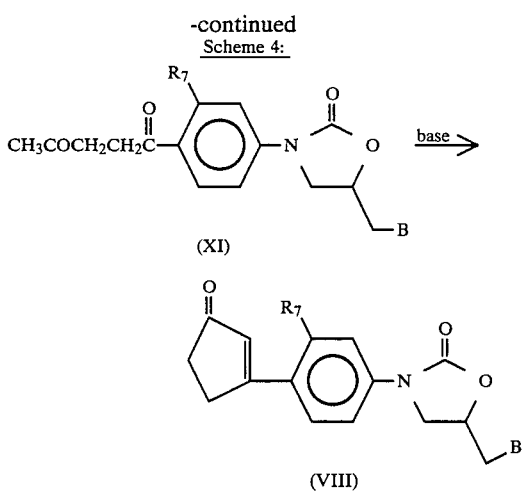

Compounds of Formula (IX) which are prepared by the process described in published European Patent Applications 127,902 and 184,170 can be converted into diketoester (X) by reaction with the anion of t-butyl acetoacetate in an aprotic solvent such as THF or DMF. Suitable bases to generate the anion include sodium hydride, potassium hydride, or potassium t-butoxide. The reaction is carried out from 0° to room temperature. Compounds (X) can be decarboxylated upon treatment with refluxing aqueous hydrochloric acid.

Finally a suitable base such as proline, morpholine, pyrrolidine, or potassium t-butoxide can be used to convert diketone (XI) into (VIII). Solvents such as benzene, toluene, or t-butanol can be used. The reaction temperature may be from room temperature to 130° C.

Compounds of Formula (VIII) can be used to prepare lactones (XII) or lactams (XIII) (Scheme 5).

Methylene chloride, dioxane, chloroform, or THF may be used as solvents and the reaction temperature can be from 0° to 80° C. Bayer-Villiger oxidation of (XIV) with either trifluoroperacetic acid or m-chloroperbenzoic acid (MCPBA) in solvents such as methylene chloride, benzene, or THF at temperatures from 0° to 80° C. followed by treatment of the resulting oxidation products with a base such as pyridine, triethylamine, or 1,8-diazabicyclo[5.4.0]undec-7-ene (DBU) in solvents such as methylene chloride, benzene, toluene, or THF at room temperature to 110° C. may convert (XIV) into the desired lactones (XII).

Treatment of (VIII) with hydroxyamine hydrochloride in the presence of a base such as pyridine or triethylamine in an alcoholic solvent such as methanol or ethanol at room temperature to 100° C. gives the corresponding oxime which undergoes a Beckmann rearrangement upon treatment with phosphorous pentachloride in a solvent such as benzene or toluene at room temperature to 110° C. to afford the desired lactams (XIII).

By using the same procedures shown in Scheme 5, 7-membered ring lactones and lactams can be obtained from 6-membered enones which are prepared by the procedure described in Example 68 which follows.

Compounds of Formula (I) wherein $R_1$ is taken together with $R_2$ to form a 5-membered ring of formula (XV) may be prepared according to

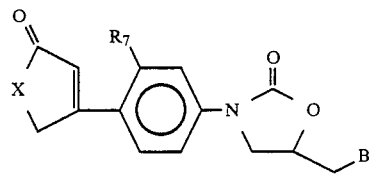

Scheme 5:

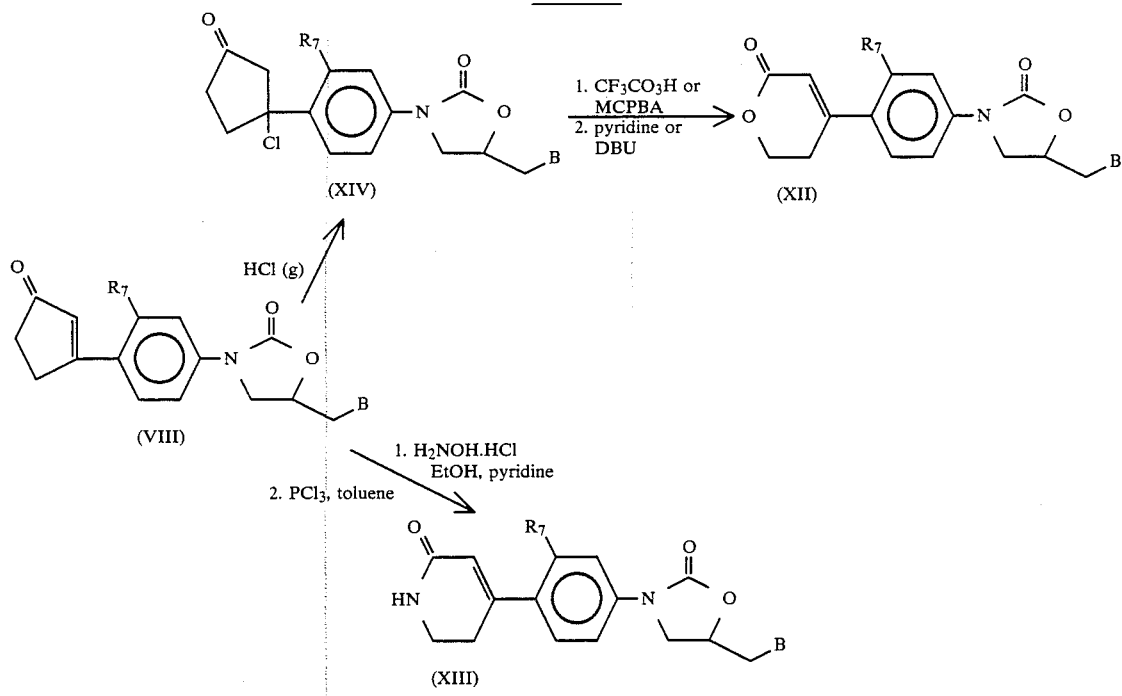

Compounds of Formula (XIV) may be derived from reaction of gaseous hydrogen chloride with (VIII).

(XV, wherein X = O, S, or NH)

synthetic Scheme 6.

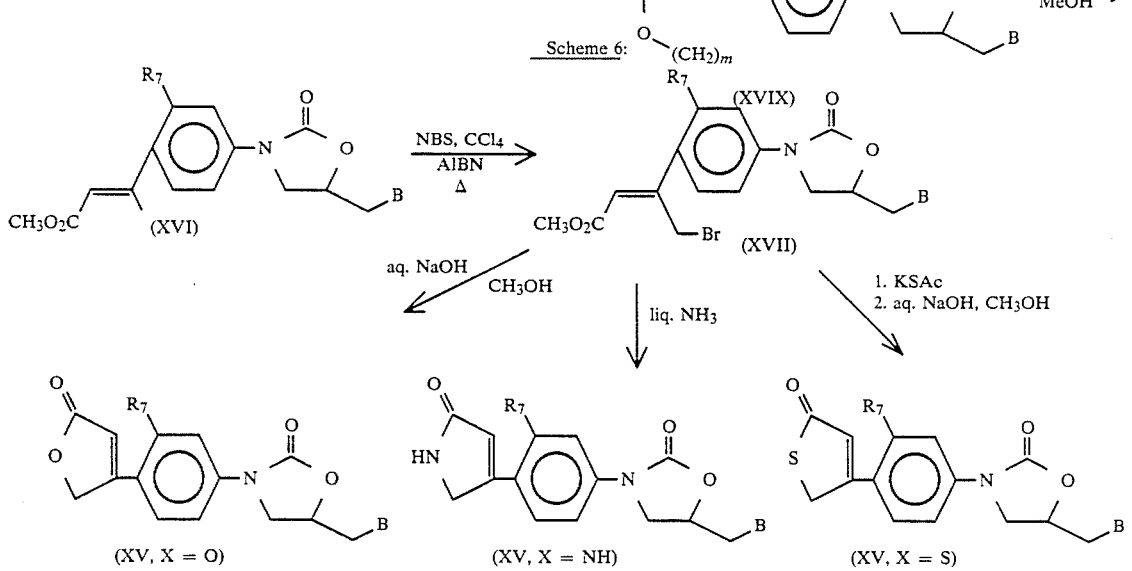

Compounds of Formula (XVI) are prepared according to the procedure described in Example 58 which follows. Treatment of (XVI) with N-bromosuccinimide (NBS) in refluxing carbon tetrachloride in the presence of a radical initiator such as azobisisobutyronitrile (AIBN) or benzoyl peroxide yields the bromide (XVII). Hydrolysis of (XVII) with aqueous sodium hydroxide or potassium hydroxide in an alcoholic solvent such as methanol or ethanol at room temperature gives lactones (XV, X=O). Liquid ammonia converts (XVII) into lactams (XV, X=NH). The reaction temperature may be from 0° to 100° C. Treatment of (XVII) with potassium thioacetate (KSAc) or thioacetic acid in the presence of triethylamine in a solvent such as acetonitrile, THF, or DMF at 0° C. to room temperature followed by hydrolysis of the resulting products with aqueous base such as sodium hydroxide or potassium hydroxide in an alcoholic solvent such as methanol or ethanol at 0° to room temperature gives thiolactones (XV, X=S).

Compounds of Formula (I) where $R_1$ is taken together with $R_2$ to form a 6 or 7-membered ring of formula (XVIII) may be prepared according to Scheme 7.

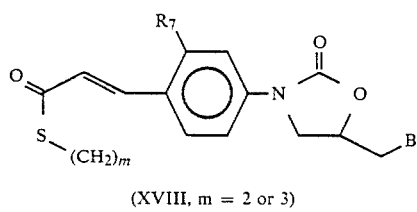

(XVIII, m = 2 or 3)

Scheme 7:

Treatment of lactones (XVIX) with sodium methoxide in methanol at room temperature to 80° C. gives the hydroxy esters (XX). The hydroxy group in (XX) is converted into mesylate or tosylate with mesyl chloride (MsCl) or tosyl chloride in pyridine at room temperature. The mesylate or tosylate is then displaced with potassium thioacetate (KSAc) or thioacetic acid in the presence of triethylamine in a solvent such as acetonitrile, THF, or DMF at 0° to 50° C. to give (XXI). Hydrolysis of (XXI) with aqueous sodium hydroxide or potassium hydroxide in an alcoholic solvent such as methanol or ethanol at 0° C. to room temperature yields the desired compound (XVIII, m=2 or 3).

Compounds of Formula (I) where R₁ is taken together with R₂ to form a 5, 6 or 7-membered ring and R₃ is a cyano group of formula (XXII):

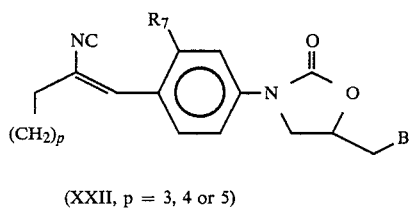

(XXII, p = 3, 4 or 5)

may be prepared by the synthetic transformations shown in Scheme 8.

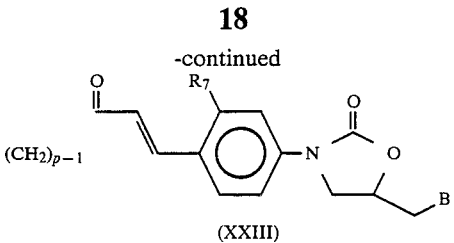

(XXIII)

iodoenones or bromoenones (XXVI) in the presence of tetrakis(triphenylphosphine)palladium(O) or bis(triphenylphosphine)palladium(II) chloride in a solvent such as THF, benzene, toluene, or DMF at room temperature to 60° C. to give (XXIII).

Wolff-Kishner reduction of (XXIII) using hydrazine hydrate and potassium hydroxide in diethylene glycol at 150° to 200° C. gives (XXIV). Hydroboration of Scheme 8:

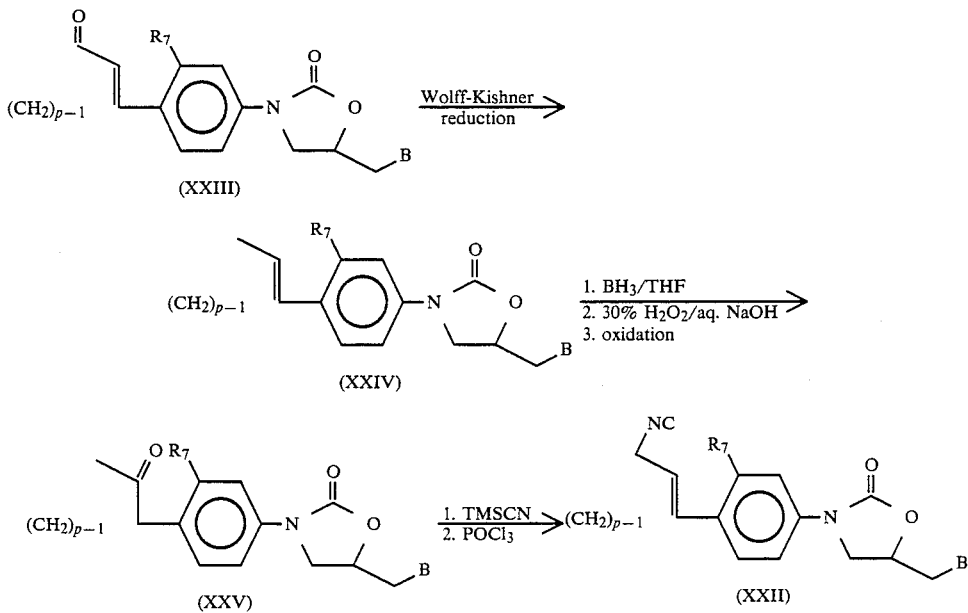

Compounds of Formula (XXIII) where p is 3 and 4 are prepared by the process described in Scheme 4 previously and Example 68 which follows. Alternatively, compounds (XXIII, p=3, 4 or 5) may be prepared according to Scheme 9. Thus, compounds (V) may react with Scheme 9:

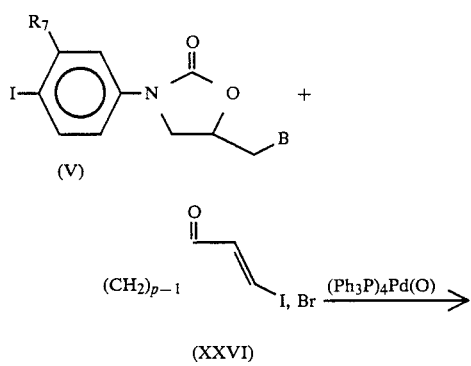

(XXIV) with diborane in THF or ether at 0° C. to room temperature followed by treatment with hydrogen peroxide in the presence of aqueous sodium hydroxide at room temperature to 70° C. and the resulting alcohols oxidized with a suitable oxidizing agent such as pyridinium chlorochromate, pyridinium dichlorochromate, or chromium trioxide in methyl chloride, DMF, or pyridine yields (XXV). Treatment of (XXV) with trimethylsilyl cyanide (TMSCN) in THF, acetonitrile, or methylene chloride at 0° to 50° C. followed by dehydration with phosphorus oxychloride at 0° C. to room temperature gives (XXII).

Pharmaceutically suitable salts of compounds of Formula (I) can be prepared in a number of ways known in the art. Where B is NH₂, pharmaceutically suitable salts include those resulting from treatment with acetic, hydrochloric, sulfuric, phosphoric, succinic, fumaric, ascorbic, and glutaric acid.

EXAMPLE 1

Preparation of
(l)-N-[3-[4-(E-1-Methyl-2-cyanoethenyl)phenyl]-2-oxooxazolidin-5-ylmethyl]acetamide (I; $R_1$=$CH_3$, $R_2$=CN, $R_3$=$R_7$=H, B=$NHCOCH_3$)

A 100 mL 3-necked flask under nitrogen was charged with 0.452 g (11.3 mmol) of sodium hydride (60% dispersion in mineral oil) and 10 mL of dry DMF. The flask was cooled to 5° C. and 2.0 g (11.3 mmol) of diethyl cyanomethylphosphonate was added dropwise over 15 minutes. The solution was stirred for 30 minutes after hydrogen evolution was complete and then 2.5 g (9.05 mmol) of (l)-N-[3-(4-acetylphenyl-2-oxooxazolidin-5-ylmethyl]acetamide was added as a solid. The reaction was allowed to warm to room temperature and stirred overnight. It was then poured onto 40 g of ice and the mixture was extracted with chloroform and the chloroform solution was dried over magnesium sulfate. The solvent was removed under reduced pressure and the solid residue was recrystallized from acetonitrile to give 1.6 g (59%) of (l)-N-[3-[4-(E-1-methyl-2-cyanoethenyl)phenyl-2-oxooxazolidin-5-ylmethyl]acetamide as a colorless crystalline solid, m.p. 176.0°–177.0° C. The geometry of the product was shown to be E by nmr analyses. The Z-isomer was isolated from the mother liquor of recrystallization and purified by liquid chromatography.

EXAMPLE 2

Preparation of
(l)-N-[3-[4-(E-2-Cyanoethenyl)phenyl]-2-oxooxazolidin-5-ylmethyl]acetamide (I; $R_1$=$R_3$=$R_7$=H, $R_2$=CN, B=$NHCOCH_3$)

To a solution of 0.742 g (4.2 mmol; 10% excess) of diethyl cyanophosphonate in 30 mL of THF was added 2.6 mL of n-butyllithium solution (1.6M in hexane) dropwise at below 5° C., and then it was allowed to stir at room temperature for 10 minutes. The mixture was cooled to 0° C. and 1 g (3.81 mmol) of (l)-N-[3-(4-formylphenyl)-2-oxooxazolidin-5-ylmethyl]acetamide was added in one portion. After the mixture was allowed to warm to room temperature and stirred for 1 hour, 5 g of ice was added and the volatile solvents were removed under reduced pressure. The resulting residue was triturated in water to give 0.9 g of solid which was filtered and recrystallized from 40 mL of ethanol with the help of activated charcoal to give 0.6 g (55%) of (l)-N-[3-[4-(E-2-cyanoethenyl)phenyl]-2-oxooxazolidin-5-ylmethyl]acetamide as a colorless crystalline solid, m.p. 189°–190° C.

By using the procedures described in Examples 1 and 2, additional cyano compounds which were prepared or can be prepared are illustrated in Table I.

TABLE I

| EX. | $R_1$ | $R_2$ | $R_3$ | $R_7$ | B | isomer | m.p. (°C.) |
|---|---|---|---|---|---|---|---|
| 1 | $CH_3$ | NC— | H | H | $NHCOCH_3$ | l | 176–177 |
| 2 | H | NC— | H | H | $NHCOCH_3$ | l | 189–190 |
| 3 | $CH_3$ | NC— | H | $CH_3$ | $NHCOCH_3$ | l | 150–151 |
| 4 | $CH_3$ | NC— | H | H | $NHCOCH_3$ | dl | |
| 5 | $C_6H_5$ | NC— | H | H | $NHCOCH_3$ | dl | |
| 6 | p-$FC_6H_4$ | NC— | H | H | $NHCOCH_3$ | l | 217–219 |
| 7 | $C_2H_5$ | NC— | H | H | $NHCOCH_3$ | l | |
| 8 | n-$C_3H_7$ | NC— | H | H | $NHCOCH_3$ | l | |
| 9 | $CH_3$ | NC— | $CH_3$ | H | $NHCOCH_3$ | l | 52–59 |
| 10 | $CH_3$ | NC— | $CH_3$ | H | $NHCOCH_3$ | dl | |
| 11 | $CH_3$ | $CH_3$ | NC— | H | $NHCOCH_3$ | l | 146–149 |
| 12 | H | NC— | $CH_3$ | H | $NHCOCH_3$ | l | |
| 13 | $CH_3$ | H | NC— | H | $NHCOCH_3$ | l | |
| 14 | $CF_3$ | NC— | H | F | $NHCO_2CH_3$ | l | |
| 15 | $CH_3$ | NC— | H | OH | $NHCO_2CH_3$ | l | |
| 16 | $CH_3$ | H | NC— | $C_2H_5$ | NHCO—◁ | l | |
| 17 | H | NC— | H | H | $N_3$ | l | |
| 18 | $CH_3$ | NC— | H | H | $NH_2$ | l | |

EXAMPLE 19

Preparation of
(l)-N-[3-[4-(E-Nitroethenyl)phenyl]-2-oxooxazolidin-5-ylmethyl]acetamide (I, $R_1$=$R_3$=$R_7$=H, $R_2$=$NO_2$, B=$NHCOCH_3$)

PART A: Preparation of (l)-N-[3-(4-Iodophenyl)-2-oxooxazolidin-5-ylmethyl]acetamide To a mixture containing 23.4 g (0.1 mol) of (l)-N-(3-phenyl-2-oxooxazolidin-5-ylmethyl)acetamide and 29 g (0.13 mol) of silver trifluoroacetate, 300 mL of acetonitrile and 200 mL of chloroform was added 27 g of iodine in one portion and allowed to stir at room temperature overnight. The mixture was filtered and the filtrate was concentrated under reduced pressure to give a brown solid which was triturated with distilled water, filtered and washed thoroughly with distilled water. The resulting solid was recrystallized from 200 mL of acetonitrile (activated charcoal used) to give 27.5 g (77%) of the desired product as a colorless crystalline solid, m.p. 194.5°–195.5° C.

Part B: Preparation of (l)-N-[3-(4-Formylphenyl-2-oxooxazolidin-5-ylmethyl]acetamide A mixture containing 31 g (86 mmol) of (l)-N-[3-(4-iodophenyl)-2-oxooxazolidin-5-ylmethyl]acetamide and 10 g of tetrakis(triphenylphosphine)]palladium(0) in 400 mL of dry degassed THF was heated to 50°-55° C. under a slight positive pressure of carbon monoxide (using balloon filled with CO). While the temperature and positive pressure of carbon monoxide were being maintained, a solution of 30 mL (25% excess) of tributyltin hydride dissolved in 65 mL of dry toluene. which had previously been flushed with carbon monoxide, was added dropwise over a period of 4 hours. When the addition was complete, 8 mL more of tributyltin hydride dissolved in 65 mL of toluene was added rapidly followed by 35 mL of toluene, and the mixture was stirred at room temperature overnight. The resulting precipitate was filtered, washed three times with toluene to give 19.1 g (85%) of the desired aldehyde, m.p. 171°-172° C.

PART C:

A mixture containing 0.5 g (1.9 mmol) of (l)-N-[3-(4-formylphenyl)-2-oxooxazolidin-5-ylmethyl]-acetamide, 0.25 mL of nitromethane, 2 drops of piperidine and 5 drops of acetic acid in absolute ethanol was heated under reflux for 5 hours. The clear mixture was then allowed to stir at room temperature overnight to give deep yellow precipitate which was collected by filtration. The solid was recrystallized once from ethanol to give 0.19 g (33%) of (l)-N-[3-[4-(E-2-nitroethenyl)-phenyl]-2-oxooxazolidin-5-ylmethyl]-acetamide as a bright yellow solid, m.p. 216°-218° C.

EXAMPLE 20

Preparation of
(l)-N-[3-[4-(E-2-Nitro-2-methylethenyl)phenyl]-2-oxooxazolidin-5-ylmethyl]acetamide ($R_1=R_7=H$, $R_2=NO_2$, $R_3=CH_3$, $B=NHCOCH_3$)

A mixture of 3 g (11.4 mmol) of (l)-N-[3-(4-formylphenyl)-2-oxooxazolidin-5-ylmethyl]acetamide, 2 mL (27.8 mmol) of nitroethane, 9 drops of piperidine and 30 drops of acetic acid in 125 mL of dry benzene was heated under reflux overnight while water formed from the reaction was removed using a Dean-Stark trap. When the clear reaction mixture was allowed to cool to room temperature, fine yellow precipitate formed. The mixture was diluted with 150 mL of ether, and the solid was collected and recrystallized from a chloroform/n-butyl chloride mixture to give 2.7 g (74%) of the desired product as a bright yellow crystalline solid, m.p. 151.5°-152.5° C.

EXAMPLE 21

Preparation of
(l)-N-[3-(4-(2-Cyano-2-methylsulfenylethenyl)phenyl]-2-oxooxazolidin-5-ylmethyl]acetamide (I; $R_1=R_7=H$, $R_2=CN$, $R_3=CH_3SO$, $B=NHCOCH_3$)

Methylsulfenylacetonitrile was prepared by adding in small portions 4.6 g (23 mmol) of m-chloroperbenzoic acid to a stirred solution of 2 g (23 mmol) of methylthioacetonitrile in 50 mL of methylene chloride at $-20°$ C. When the oxidation was complete as shown by starch-iodide paper test, the solvent was removed under reduced pressure, and the solid residue was triturated with 18 mL of water. The mixture was filtered and water from the aqueous filtrate was removed under reduced pressure to give 2.19 g of the sulfoxide as a colorless solid. When the reaction was carried out at room temperature using an excess of m-chloroperbenzoic acid, methylsulfonylacetonitrile was obtained.

A mixture containing 1 g (3.8 mmol) of (l)-N-[3-(4-formylphenyl)-2-oxooxazolidin-5-ylmethyl]acetamide, 0.4 g (3.8 mmol) of methylsulfenylacetonitrile, 3 drops of piperidine and 10 drops of acetic acid in 50 mL of dry benzene was heated under reflux overnight and the water formed during the reaction was removed using a Dean-Stark trap. Solid precipitate obtained on cooling was collected by filtration and recrystallized once from a n-butyl chloride/acetonitrile mixture (activated charcoal) to give 0.74 g (83%) of the desired product as a pale yellowish solid, m.p. 158.5°-160° C.

By using the procedures of Examples 19-25, the following compounds in Table II were prepared or can be prepared.

TABLE II

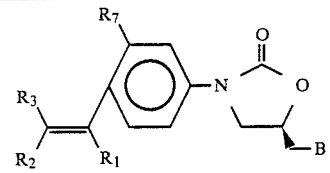

| Ex. | $R_1$ | $R_2$ | $R_3$ | $R_7$ | B | isomer | m.p. (°C.) |
|---|---|---|---|---|---|---|---|
| 19 | H | $-NO_2$ | H | H | $NHCOCH_3$ | l | 216-218 |
| 20 | H | $-NO_2$ | $CH_3$ | H | $NHCOCH_3$ | l | 151.5-152.5 |
| 21 | H | NC— | $CH_3SO$ | H | $NHCOCH_3$ | l | 158.5-160 |
| 22 | H | $-CO_2C_2H_5$ | H | H | $NHCOCH_3$ | l | 135-136 |
| 23 | $CH_3$ | $-CONH_2$ | H | H | $NHCOCH_3$ | l | 203-204 |
| 24 | H | $-SOCH_3$ | H | H | $NHCOCH_3$ | l | 62-69 |
| 25 | J | $-CHO$ | H | H | $NHCOCH_3$ | l | 203-204 |
| 26 | H | NC— | NC— | H | $NHCOCH_3$ | l | 188.5-190.0 |
| 27 | H | NC— | $-SO_2CH_3$ | H | $NHCOCH_3$ | l | 222-223 |
| 28 | H | Ac | Ac | H | $NHCOCH_3$ | l | 151-152 |
| 29 | H | $-NO_2$ | $C_2H_5$ | H | $NHCOCH_3$ | l | 155-156 |
| 30 | H | $-NO_2$ | n-$C_3H_7$ | H | $NHCOCH_3$ | l | 132.5-133.5 |
| 31 | H | $-SO_2CH_3$ | $-CO_2C_2H_5$ | H | $NHCOCH_3$ | l | 151.5-152.5 |
| 32 | H | $-SOCH_3$ | $-CO_2C_2H_5$ | H | $NHCOCH_3$ | l | 95-99 |
| 33 | H | $-NO_2$ | $CF_3$ | $CH_3$ | NHCO—◁ | l | |
| 34 | H | NC— | $-SO_2CH_3$ | F | $NHCO_2CH_3$ | l | |
| 35 | H | Ac | Ac | OH | $NHSOCH_3$ | l | |

TABLE II-continued

[Structure: phenyl ring with $R_7$ at one position, $R_3$, $R_2$, $R_1$ on a vinyl group, and an N-linked 2-oxooxazolidine ring with substituent B at the 5-position]

| Ex. | $R_1$ | $R_2$ | $R_3$ | $R_7$ | B | isomer | m.p. (°C.) |
|-----|-------|-------|-------|-------|---|--------|------------|
| 36 | H | —$NO_2$ | $C_2H_5$ | $C_2H_5$ | $N_3$ | l | |
| 37 | H | NC— | NC— | H | $NCH_3COCH_3$ | l | |

EXAMPLE 22

Preparation of
(l)-N-[3-[4-(E-2-Carboethoxyethenyl)-phenyl]-2-oxooxazolidin-5-ylmethyl]acetamide (I; $R_1$=$R_3$=$R_7$=H, $R_2$=—$CO_2C_2H_5$, B=$NHCOCH_3$)

To a slurry of 0.175 g (4.38 mmol) of sodium hydride (60% dispersion in mineral oil) in 10 mL of DMF was added 0.984 g (4.38 mmol) of triethyl phosphonoacetate dropwise at 0° to 5° C. over a period of 15 minutes. The mixture was stirred for 30 minutes after the evolution of hydrogen subsided, and 1 g (3.8 mmol) of (l)-N-[3-(4-formylphenyl)-2-oxooxazolidin-5-ylmethyl]acetamide was added in one portion. The reaction was allowed to warm to room temperature and stirred overnight. About 5 mL of ice water was added, the mixture was concentrated under reduced pressure and the residue was recrystallized from an isopropanol-methylene chloride mixture to give 0.25 g (22%) of (l)-N-[3-[4-(E-2-carboethoxyethenyl)phenyl]-2-oxooxazolidin-5-ylmethyl]acetamide as a colorless solid, m.p. 135.0°–136.0° C.

EXAMPLE 23

Preparation of
(l)-N-[3-[4-(E-1-Methyl-2-carbamidoethenyl)phenyl]-2-oxooxazolidin-5-ylmethyl]acetamide (I; $R_1$=$CH_3$, $R_2$=—$CONH_2$, $R_3$=$R_7$=H, B=$NHCOCH_3$)

The copper(0) catalyst was prepared by the procedure described in Ravindranathan et. al., *J. Org. Chem.*, 47, 4812 (1982). A mixture containing 6.0 g of the copper(0) catalyst, 4.8 g (16 mmol) of (l)-N-[3-[4-(E-1-methyl-2-cyanoethenyl)phenyl-2-oxooxazolidin-5-ylmethyl]acetamide (I; $R_1$=$CH_3$, $R_2$=CN, $R_3$=$R_7$=H, B=$NHCOCH_3$), 100 mL of water and 100 mL of glyme was heated under reflux under nitrogen atmosphere for 8 hours. The catalyst was removed by filtration while still hot, and the filtrate was concentrated under reduced pressure to give a white solid which was purified by flash column chromatography on silica gel to give 3.98 g (78%) of (l)-N-[3-[4-(E-1-methyl-2-carbamidoethenyl)phenyl]-2-oxooxazolidin-5-ylmethyl]-acetamide, m.p. 203.0°–204.0° C.

EXAMPLE 24

Preparation of
(l)-N-[3-[4-(2-Methylsulfenylethenyl)-phenyl]-2-oxooxazolidin-5-ylmethyl]acetamide (I; $R_1$=$R_3$=$R_7$=H, $R_2$=—$SOCH_3$, B=$NHCOCH_3$)

To a solution of 1.22 g (5.72 mmol) of methylsulfenylmethyldiethylphosphonate [prepared by the procedure in M. Nikolajczyk and A. Zaotorski. *Synthesis*, 669 (1973)] in 10 mL of THF cooled at −78° C. was added 3.57 mL (5.72 mmol) of n-butyllithium (1.6M in hexane). After stirring for 2 hours, 1.5 g (5.72 mmol) of (l)-N-[3-(4-formylphenyl)-2-oxooxazolidin-5-ylmethyl]acetamide dissolved in THF was added dropwise and stirred for 3 hours after the addition was complete. The mixture was then allowed to warm to room temperature and stirred for several more hours. The solvent was removed under reduced pressure and the resulting residue was dissolved in water and extracted thoroughly with methylene chloride. After drying, the solvent was removed and the crude residue was purified by flash column chromatography on silica gel to give 275 mg (15%) of (l)-N-[3-[4-(2-methylsulfenylethenyl)-phenyl]-2-oxooxazolidin-5-ylmethyl]acetamide as a colorless solid, m.p. 62°–69° C.

EXAMPLE 25

Preparation of
(l)-N-[3-[4-(E-2-Formylethenyl)phenyl]-2-oxooxazolidin-5-ylmethyl]acetamide (I; $R_1$=$R_3$=$R_7$=H, $R_2$=CHO, B=$NHCOCH_3$)

To 5 g (11.6 mmol) of (1,3-dioxolan-2-ylmethyl)-triphenylphosphonium bromide in 200 mL of glyme was added 7.5 mL of 1.55M n-BuLi at 0° C., then the mixture was stirred at room temperature for 1 hour. To the mixture was added 3 g (11.4 mmol) of (l)-N-[3-(4-formylphenyl)-2-oxooxazolidin-5-ylmethyl]acetamide in one portion at 0° C., slowly heated to reflux for 1 hour and stirred at room temperature overnight. The resulting dark brown, almost clear solution with small amount of brown gum at the bottom was stripped, triturated with ether followed by water and dissolved in 100 mL of acetone. Ten drops of 6M HCl was added to the solution and stirred at room temperature for 1 hour. The mixture was evaporated to dryness under reduced pressure, triturated with water to give a tan/brown solid which was treated with 10 mL of acetonitrile (not very soluble) and diluted with 100 mL of ether to give 0.99 g of a tan solid. It was recrystallized once from 20 mL of acetonitrile (with activated charcoal) to give 0.71 g (22%) of (l)-N-[3-[4-(E-2-formylethenyl)phenyl]-2-oxooxazolidin-5-ylmethyl]acetamide as light tan needles, m.p. 203°–204° C.

By using the procedure of Example 25, the following compounds shown in Table III can be prepared.

TABLE III

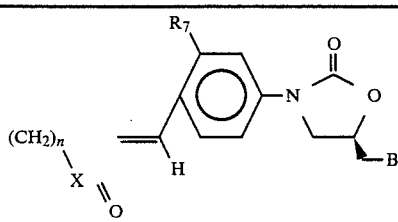

| Ex. | R7 | B | n. | X | isomer | m.p. (°C.) |
|---|---|---|---|---|---|---|
| 38 | H | NHCOCH3 | 2. | CH2 | E. 1 | 207–208 |
| 39 | CH3 | NHCOCH3 | 3. | CH2 | E. 1 | |
| 40 | H | NHCOCH3 | 3. | CH2 | E. 1 | 118–121 |
| 41 | H | NHCOCH3 | 2. | O | E. 1 | 119–122 |
| 42 | OH | NHCOCH3 | 3. | O | E. 1 | |
| 43 | H | NHCOCH3 | 4. | O | E. 1 | |
| 44 | H | NHCOCH3 | 2. | S | E. 1 | |
| 45 | CH3 | NH2 | 3. | S | E. 1 | |
| 46 | F | NHCOCH3 | 4. | S | E. 1 | |
| 47 | H | NHCOCH3 | 2. | NH | E. 1 | |
| 48 | CH3 | NHCOCH3 | 3. | NH | E. 1 | |
| 49 | OH | NHCOCH3 | 4. | NH | E. 1 | |
| 50 | H | NHCO—◁ | 2. | CH2 | E. 1 | |
| 51 | CH3 | NHCO2CH3 | 3. | O | E. 1 | |
| 52 | C2H5 | NHSOCH3 | 2. | CH2 | E. 1 | |
| 53 | F | NHSOCH3 | 3. | O | E. 1 | |
| 54 | OH | N3 | 2. | S | E. 1 | |
| 55 | H | N3 | 3. | NCH3 | E. 1 | |
| 56 | H | N3 | 4. | CH2 | E. 1 | |
| 57 | H | N3 | 4. | O | E. 1 | |

EXAMPLE 58

Preparation of
(l)-N-[3-[4-(E-1-Methyl-2-carbomethoxyethenyl)-phenyl]-2-oxooxazolidin-5-ylmethyl]acetamide (I, $R_1$=CH3, $R_2$=CO2CH3, $R_3$=$R_7$=H, B=NHCOCH3)

To a mixture containing 3 g (11.4 mmol) of (l)-N-[3-(4-iodophenyl)-2-oxooxazolidin-5-ylmethyl]acetamide, 10 mL of triethylamine and 30 mL of THF under reflux was added 4 mL of methyl crotonate and 0.86 g of diacetobis(triphenyl-phosphine)palladium(II). After stirring overnight, the mixture was cooled to room temperature, diluted with ether, filtered through a bed of celite. The filtrate was concentrated under reduced pressure, the residue was taken up into methylene chloride and diluted with hexane to precipitate the crude product. The crude product was recrystallized from a methylene chloride-hexane mixture to give 1.0 g (26%) of (l)-N-[3-[4-(E-1-methyl-2-carbomethoxyethenyl)-phenyl]-2-oxooxazolidin-5-ylmethyl]acetamide as a white solid, m.p. 173°–178° C.

By using the procedure described in Example 58, the following compounds in Table IV were prepared or can be prepared.

TABLE IV

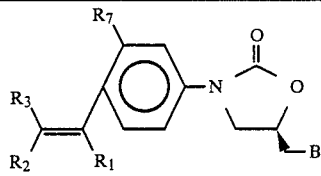

| Ex. | R1 | R2 | R3 | R7 | B | isomer | m.p. (°C.) |
|---|---|---|---|---|---|---|---|
| 58 | CH3 | CO2CH3 | H | N | NHCOCH3 | 1 | 173–178 |
| 59 | H | CO2CH3 | H | H | NHCOCH3 | 1 | 183–185 |
| 60 | H | COCH3 | H | H | NHCOCH3 | 1 | 175–178 |
| 61 | H | CON(CH3)2 | H | H | NHCOCH3 | 1 | 228 dec |
| 62 | H | CONH2 | H | H | NHCOCH3 | 1 | 249–250 dec |
| 63 | CH3 | CO2CH3 | H | CH3 | NH2 | 1 | |
| 64 | CH3 | CONH2 | H | C2H5 | NHCO2CH3 | 1 | |
| 65 | CH3 | COCH3 | H | F | NHSOCH3 | 1 | |
| 66 | CH3 | CO2CH3 | H | OH | NCH3COCH3 | 1 | |
| 67 | CH3 | CO2CH3 | H | H | N3 | 1 | |

EXAMPLE 68

Preparation of
(l)-N-[3-[4-(3-oxo-1-cyclohexen-1-yl)-phenyl)]-2-oxooxazolidin-5-ylmethyl]acetamide (I, $R_1$—$R_2$=(CH2)3CO, $R_3$=$R_7$=H, B=NHCOCH3)

PART A: Preparation of (l)-N-[3-[4-(3-Dimethylamino-1-oxopropyl)phenyl]-2-oxooxazolidin-5-ylmethyl]acetamide To 20 mL of trifluoroacetic acid at 0°–5° C. under nitrogen in an ice-bath was added 2.70 mL of N,N,N',N'-tetramethyldiaminomethane and then 5.0 g of (l)-N-[3-[4-(1-oxoethyl)phenyl]-2-oxooxazolidin-5-ylmethyl]-acetamide. The mixture was allowed to warm to room temperature, then heated at 50° C. for 24 hours. The mixture was cooled to room temperature and diluted with water and adjusted to pH 7 by addition of 5% NaHCO3 solution. The product was extracted into ethyl acetate which was dried (MgSO4) and evaporated in vacuo to give 3.30 g (55%) of the product.

PART B

To 0.48 g of 50% sodium hydride in mineral oil (washed free of the oil by decantation with petroleum ether) under nitrogen was added 10 mL of glyme and then by pipette 1.10 mL of methyl acetoacetate. The mixture was stirred until hydrogen evolution ceased and all the sodium hydride had reacted, and then treated with a solution of 3.33 g of the product from Part A in 15 mL of glyme and the mixture was heated under reflux; after about 15 minutes, a bright yellow precipitate formed. The mixture was diluted with an equal volume of dry acetonitrile and heated under reflux overnight. The mixture was acidified with acetic acid and then the glyme was removed in vacuo. The residue was dissolved in ethyl acetate, filtered to remove insoluble material, which was washed with water, dried and purified by recrystallization from ethanol to give 0.15 g (5%) of (l)-N-[3-[4-(3-oxo-1-cyclohexen-1-yl)phenyl-2-oxooxazolidin-5-ylmethyl]acetamide, m.p. 205.5°–207° C., d.

By using the procedure described in Example 68 and synthesis Schemes 4–7, the following compounds can be prepared.

TABLE V $$\underset{(CH_2)_m}{\overset{R_7}{\text{structure (XXII, p = 3, 4 or 5)}}}$$

| Ex. | R₇ | B | X. | m | isomer | m.p. (°C.) |
|-----|-----|---------|------|---|--------|-----------|
| 68 | H | NHCOCH₃ | CH₂. | 2 | 1 | 205.5–207 |
| 69 | H | NHCOCH₃ | CH₂. | 1 | 1 | |
| 70 | OH | NHCOCH₃ | CH₂. | 1 | 1 | |
| 71 | F | NHCOCH₃ | CH₂. | 1 | 1 | |
| 72 | H | NHCOCH₃ | O. | 1 | 1 | |
| 73 | H | NHCOCH₃ | O. | 2 | 1 | |
| 74 | H | NHCOCH₃ | O. | 3 | 1 | |
| 75 | CH₃ | NHSOCH₃ | S. | 1 | 1 | |
| 76 | C₂H₅ | NHCO₂CH₃ | S. | 2 | 1 | |
| 77 | OH | N₃ | S. | 3 | 1 | |
| 78 | H | NHCO—▷ | NH. | 1 | 1 | |
| 79 | H | NCH₃COCH₃ | NH. | 2 | 1 | |
| 80 | H | NHCOCH₃ | NH. | 3 | 1 | |
| 81 | F | NH₂ | NH. | 1 | 1 | |
| 82 | OH | NHCOCH₃ | NH. | 2 | 1 | |

By using the procedure described in synthesis discussion Scheme 8, the following compounds can be prepared.

TABLE VI $$\underset{(CH_2)_p}{\overset{R_7}{\text{NC structure (XXII, p = 3, 4 or 5)}}}$$

| Ex. | R₇ | B | p | isomer | m.p. (°C.) |
|-----|-----|-----------|---|--------|-----------|
| 83 | H | NHCOCH₃ | 3 | 1 | |
| 84 | H | NHCOCH₃ | 4 | 1 | |
| 85 | H | NHCOCH₃ | 5 | 1 | |
| 86 | CH₃ | NHCO₂CH₃ | 3 | 1 | |
| 87 | OH | NHSOCH₃ | 4 | 1 | |
| 88 | F | N₃ | 5 | 1 | |
| 89 | C₂H₅ | NH₂ | 3 | 1 | |
| 90 | H | NCH₃COCH₃ | 4 | 1 | |

Dosage Forms

The antibacterial agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. Usually a daily dosage of active ingredient can be about 5 to 20 milligrams per kilogram of body weight. Ordinarily, when the more potent compounds of this invention are used, 5 to 15, and preferably 5 to 7.5 milligrams per kilogram per day, given in divided doses 2 to 4 times a day or in sustained release form, is effective to obtain desired results. These drugs may also be administered parenterally.

Projected therapeutic levels in humans should be attained by the oral administration of 5–20 mg/kg of body weight given in divided doses two to four times daily. The dosages may be increased in severe or life-threatening infections.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, manitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidants such as sodium bisulfate, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules containing 75 milligrams of the active ingredient. The capsules are washed and dried.

Tablets

A large number of tablets are prepared by conventional procedures so that the dosage unit is 75 milligrams of active ingredient, 0.2 milligrams of colloidal silicon dioxide, 5 milligrams of magnesium stearate, 250 milligrams for microcrystalline cellulose, 11 milligrams of cornstarch and 98.8 milligrams of lactose. Appropriate coatings may be applied to increase palatability or delay absorption.

Injectables

A parenteral composition suitable for administration by injection is prepared by stirring 1.5% by weight of active ingredient in 10% by volume propylene glycol and water. The solution is made isotonic with sodium chloride and sterilized.

Suspensions

An aqueous suspension is prepared for oral administration so that each 5 milliliters contain 75 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Utility

Test results indicate that the novel compounds of this invention are biologically active against gram positive bacteria including multiply antibiotic resistant strains of staphylococci and streptococci. These agents are potentially useful for the treatment of both human and animal bacterial infections including diseases of the respiratory, gastrointestinal genito-urinary systems; blood; interstitial fluids; and soft tissues.

As shown in Table VII compounds of formula I exert an in vitro antibacterial effect. A standard microdilution method (National Committee for Clinical Standards. Tentative standard M7-T. Standard methods for dilution antimicrobial susceptibility tests for bacteria that grow aerobically. National Committee for Clinical Laboratory Standards, Villanova, Pa. 1982) with Mueller-Hinton broth is used to determine the 24-hour minimal inhibitory concentrations (MIC's) for test strains of Staphylococcus aureus and Escherichia coli.

The in vivo potency of these compounds is exemplified by the data summarized in Table VIII. Determinations of in vivo efficacy are performed by inoculating mice intraperitoneally with cultures of the infecting organism diluted to produce 100% mortality in control animals within twenty-four hours. The culture of S. aureus used to infect the animals was diluted to the required bacterial density using 5% aqueous hog gastric mucin. The compounds are dissolved or suspended in 0.25% aqueous Methocel ® (Methocel ®: Hydroxypropyl Methylcellulose, E15 Premium, Dow Chemical Company) for oral administration or sterile distilled water containing 5% dimethylsulfoxide (Fisher Scientific Company, Fairlawn, N.J.) for subcutaneous administration. The mice are dosed at one hour and at four hours post-infection. Mortality is recorded daily until test termination seven days post infection. The number of survivors in each treatment group on the seventh day after infection is used in the calculation of the $ED_{50}$, the dose of compound that protects 50% of the mice (Litchfield, J. T. and Wildoxon. A simplified method for evaluating dose-effect experiments. *J. Pharmacol Exp. Ther.*, 96:99–113, 1949).

TABLE VII

In Vitro Broth Microdilution Minimal Inhibitory Concentrations (MIC's)

| Ex. No. | Minimum Inhibitory Concentration (μg/ml) | |
|---|---|---|
| | Staphylococcus aureus | Escherichia coli |
| 1 | 1 | >128 |
| 2 | 4 | >128 |
| 3 | 2 | >128 |
| 5 | 32 | >128 |
| 6 | >128 | >128 |
| 7 | 1 | >128 |
| 8 | 2 | >128 |
| 9 | 2 | >128 |
| 11 | 8 | >128 |
| 12 | 1 | >128 |
| 13 | 8 | >128 |
| 19 | 8 | >128 |
| 20 | 0.1 | >128 |
| 21 | 4 | >128 |
| 22 | 8 | >128 |
| 23 | 4 | >128 |
| 24 | 8 | >128 |
| 25 | 0.5 | >128 |
| 26 | 16 | >128 |
| 27 | 16 | >128 |
| 28 | 16 | >128 |
| 29 | 1 | >128 |
| 30 | 4 | >128 |
| 31 | 16 | >128 |
| 32 | 16 | >128 |
| 58 | 2 | >128 |
| 59 | 8 | >128 |
| 60 | 4 | >128 |
| 61 | 32 | >128 |
| 62 | 32 | >128 |
| 68 | 0.5 | >128 |

TABLE VIII

In Vivo Activity of Compounds Against Staphylococcus aureus in an Acute Lethal Mouse Model

| Ex. No. | $ED_{50}$ (mg/kg) | |
|---|---|---|
| | Oral Administration | Subcutaneous Administration |
| 1 | 1.3 | 0.8 |
| 2 | 3.5 | 2.8 |
| 3 | 6.4 | 5.1 |
| 5 | >90 | >90 |
| 6 | NT | NT |
| 7 | 3.1 | 2.1 |
| 8 | >90 | >90 |
| 9 | 3.8 | 2.5 |
| 11 | NT | NT |
| 12 | 2.9 | 1.9 |
| 13 | NT | NT |
| 19 | >90 | >90 |
| 20 | 14.1 | 9.1 |
| 21 | >90 | 11.8 |
| 22 | >90 | >90 |
| 23 | 26.4 | 36.2 |
| 24 | 33.3 | 14.6 |
| 25 | >80 | >80 |
| 26 | >90 | >90 |
| 27 | >90 | >90 |
| 28 | >90 | >90 |
| 29 | >90 | >90 |
| 30 | >90 | >90 |
| 31 | >90 | >90 |
| 32 | >90 | >90 |
| 58 | NT | 46.2 |
| 59 | NT | >90 |

TABLE VIII-continued

In Vivo Activity of Compounds Against *Staphylococcus aureus* in an Acute Lethal Mouse Model

| Ex. No. | ED$_{50}$ (mg/kg) | |
|---|---|---|
| | Oral Administration | Subcutaneous Administration |
| 60 | NT | 51.9 |
| 61 | NT | 39.5 |
| 62 | NT | 20.4 |
| 68 | 2.4 | 1.7 |

NT = Not Tested

What is claimed is:

1. A compound having the formula:

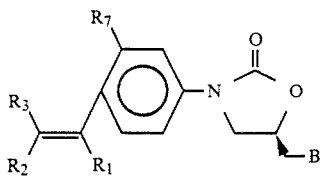 (I)

wherein for the l isomer or racemic mixtures containing it
m is 1, 2 or 3;
n is 2, 3 or 4;
p is 3, 4 or 5; and
X is CH$_2$ or a pharmaceutically suitable salt thereof.

2. A compound of claim 1 wherein B is

where R$_5$ is H, CH$_3$, OR$_6$, CHCl$_2$, CH$_2$Cl, CH$_2$OH or CH$_2$OCH$_3$ where R$_6$ is defined in claim 1.

3. A compound of claim 1 wherein R$_1$ independently is H or alkyl of 1–3 carbon atoms, or is taken together with R$_2$ to form a 5- or 6-membered ring of the formula:

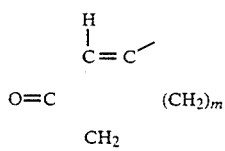

where m is 1 or 2.

4. A compound of claim 1 wherein R$_2$ independently is an electron-withdrawing group.

5. A compound of claim 1 wherein R$_3$ independently is H, alkyl of 1–3 carbon atoms, or phenyl.

6. A compound of claim 1 wherein:
(a) B is —NHCR$_5$ where R$_5$ is H, CH$_3$, OR$_6$, CHCl$_2$, CH$_2$Cl, CH$_2$OH or CH$_2$OCH$_3$ where R$_6$ is defined in claim 1.
(b) R$_1$ independently is H or alkyl of 1–3 carbon atoms, or is taken together with R$_2$ to form a 5- or 6-membered ring of the formula:

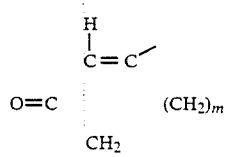

where m is 1 or 2.
(c) R$_2$ independently is an electron-withdrawing group having a sigma value greater than about 0.2.
(d) R$_3$ independently is H, alkyl of 1–3 carbon atoms, or phenyl.

7. A compound of claim 1 wherein B is

8. A compound of claim 1 wherein R$_2$ independently is CN or NO$_2$.

9. A compound of claim 1 wherein R$_3$ independently is H, CH$_3$ or C$_2$H$_5$.

10. A compound of claim 1 wherein:
(a) B is

(b) R$_1$ independently is H, CH$_3$ or C$_2$H$_5$, or is taken together with R$_2$ to form a 5- or 6-membered ring of the formula:

where m is 1 or 2;
(c) R$_2$ independently is CN or NO$_2$; and
(d) R$_3$ independently is H, CH$_3$ or C$_2$H$_5$.

11. The compound of claim 1 which is (l)-N-[3-[4-(E-1-methyl-2-cyanoethenyl)-phenyl]-2-oxooxazolidin-5-ylmethyl]acetamide.

12. The compound of claim 1 which is (l)-N-[3-[4-(3-oxo-1-cyclohexen-1-yl)phenyl]-2-oxooxazolidin-5-ylmethyl]acetamide;

13. The compound of claim 1 which is (l)-N-[3-[4-(E-2-nitroethenyl)phenyl]-2-oxooxazolidin-5-ylmethyl]acetamide.

14. The compound of claim 1 which is (l)-N-[3-[4-(E-1-methyl-2-nitroethenyl)phenyl]-2-oxooxazolidin-5-ylmethyl]acetamide 15. A pharmaceutical composition containing essentially of a pharmaceutically suitable carrier and an antibacterial effective amount of a compound of claim 1.

16. A pharmaceutical composition containing essentially of a pharmaceutically suitable carrier and an antibacterial effective amount of a compound of claim 2.

17. A pharmaceutical composition containing essentially of a pharmaceutically suitable carrier and an antibacterial effective amount of a compound of claim 3.

18. A pharmaceutical composition containing essentially of a pharmaceutically suitable carrier and an antibacterial effective amount of a compound of claim 4.

19. A pharmaceutical composition containing essentially of a pharmaceutically suitable carrier and an antibacterial effective amount of a compound of claim 5.

20. A pharmaceutical composition containing essentially of a pharmaceutically suitable carrier and an antibacterial effective amount of a compound of claim 6.

21. A pharmaceutical composition containing essentially of a pharmaceutically suitable carrier and an antibacterial effective amount of a compound of claim 7.

22. A pharmaceutical composition containing essentially of a pharmaceutically suitable carrier and an antibacterial effective amount of a compound of claim 8.

23. A pharmaceutical composition containing essentially of a pharmaceutically suitable carrier and an antibacterial effective amount of a compound of claim 9.

24. A pharmaceutical composition containing essentially of a pharmaceutically suitable carrier and an antibacterial effective amount of a compound of claim 10.

25. A pharmaceutical composition containing essentially of a pharmaceutically suitable carrier and an antibacterial effective amount of the compound of claim 11.

26. A pharmaceutical composition containing essentially of a pharmaceutically suitable carrier and an antibacterial effective amount of the compound of claim 12.

27. A pharmaceutical composition containing essentially of a pharmaceutically suitable carrier and an antibacterial effective amount of the compound of claim 13.

28. A pharmaceutical composition containing essentially of a pharmaceutically suitable carrier and an antibacterial effective amount of the compound of claim 14.

29. A method for alleviating bacterial infection in a mammal which comprises administering to the mammal an antibacterial effective amount of a compound of claim 1.

30. A method for alleviating bacterial infection in a mammal which comprises administering to the mammal an antibacterial effective amount of a compound of claim 2.

31. A method for alleviating bacterial infection in a mammal which comprises administering to the mammal an antibacterial effective amount of a compound of claim 3.

32. A method for alleviating bacterial infection in a mammal which comprises administering to the mammal an antibacterial effective amount of a compound of claim 4.

33. A method for alleviating bacterial infection in a mammal which comprises administering to the mammal an antibacterial effective amount of a compound of claim 5.

34. A method for alleviating bacterial infection in a mammal which comprises administering to the mammal an antibacterial effective amount of a compound of claim 6.

35. A method for alleviating bacterial infection in a mammal which comprises administering to the mammal an antibacterial effective amount of a compound of claim 7.

36. A method for alleviating bacterial infection in a mammal which comprises administering to the mammal an antibacterial effective amount of a compound of claim 8.

37. A method for alleviating bacterial infection in a mammal which comprises administering to the mammal an antibacterial effective amount of a compound of claim 9.

38. A method for alleviating bacterial infection in a mammal which comprises administering to the mammal an antibacterial effective amount of a compound of claim 10.

39. A method for alleviating bacterial infection in a mammal which comprises administering to the mammal an antibacterial effective amount of the compound of claim 11.

40. A method for alleviating bacterial infection in a mammal which comprises administering to the mammal an antibacterial effective amount of the compound of claim 12.

41. A method for alleviating bacterial infection in a mammal which comprises administering to the mammal an antibacterial effective amount of the compound of claim 13.

42. A method for alleviating bacterial infection in a mammal which comprises administering to the mammal an antibacterial effective amount of the compound of claim 14.

* * * * *